United States Patent [19]

Davidson

[11] Patent Number: 4,846,173
[45] Date of Patent: Jul. 11, 1989

[54] ANTERIOR-LATERAL "OFF-AXIS BITE BLOCK SYSTEM" FOR RADIATION THERAPY

[76] Inventor: Todd W. Davidson, Rt. 2, Box 281 K, Fairhope, Ala. 36532

[21] Appl. No.: 94,843

[22] Filed: Sep. 10, 1987

[51] Int. Cl.⁴ ............................................. A61B 17/00
[52] U.S. Cl. .................. 128/303 B; 378/208; 33/512
[58] Field of Search .......... 128/1 R, 303 B; 378/208, 177–180; 33/511–514

[56] References Cited

U.S. PATENT DOCUMENTS

| | | | |
|---|---|---|---|
| 3,073,310 | 1/1963 | Mocorski | 128/303 B |
| 3,221,743 | 12/1965 | Thompson et al. | 128/303 B |
| 4,279,260 | 7/1981 | Stump | 33/512 X |
| 4,526,169 | 7/1985 | Narishige et al. | 128/303 B |
| 4,722,336 | 2/1988 | Kim et al. | 128/303 B |

FOREIGN PATENT DOCUMENTS 921555 4/1982 U.S.S.R. .................. 128/303 B

Primary Examiner—Max Hindenburg
Assistant Examiner—John P. Lacyk
Attorney, Agent, or Firm—Jennings, Carter, Thompson & Veal

[57] ABSTRACT

A radiation therapy positioning device utilizes a plurality of orthogonally adjustable members to present a patient bite block for insertion in a patient's mouth during radiation therapy. The apparatus is designed to insure repeatability of positioning and maximum access to the patient for treatment from various angles.

6 Claims, 5 Drawing Sheets

ANTERIOR-LATERAL "OFF-AXIS BITE BLOCK SYSTEM" FOR RADIATION THERAPY

BACKGROUND

The present bite block systems in use today are used generally for head and neck immobilization, in order to maintain a specific position during treatments with radiation. The bite block systems are designed to maintain the head and neck in position during the treatment, and to allow replication of the same exact position. An important part of the procedure in radiation therapy is to prevent interference between the path of radiation and the patient, so that the patient receives the full benefit of the therapy. Devices presently in use present a problem, in that, the path of radiation is interfered with by the base of the devices presently in use, particularly during treatment of the areas near the back of the patient's head, otherwise known as the posterior oblique view. Several bite block systems in present use utilize a vertical support structure that is on the center line, meaning that the horizontal support structure connected to it passes directly over the face of the patient as the bite block systems is directed for placement in the patient's mouth, thus obstructing radiation treatment of the face or forehead. Other bite block system have vertical support structures that are off the center line, which provide a clear and unobstructed treatment of the face and forehead; however, obstruction occurs during treatment of the side of the head and the top of the face, otherwise known as the anterior oblique view.

Another problem occurring during use of the present devices is that the head cushions are capable of slippage from side to side on the base structure, due to faulty design. Slippage of the head cushions could allow critical and dangerous movement, causing the radiation to treat an undesired portion of the head or neck, resulting in possible serious damage to the patient.

SUMMARY OF THE INVENTION

It is an object of the present invention to provide a bite block system that assures head and neck immobilization during radiation therapy without interference between the path of radiation and the patient being treated, and to provide replication of exact treatment positions for extended periods of treatment. The anterior-lateral off-axis bite block system provides a base structure, vertical, horizontal, and lateral support structures for the bite block which is secured in the moutn of the patient. The present invention solves the problem of interference between the path of radiation and the patient by providing a that mounts interchangeably in the left superior or right superior corners of the base structure, providing an off-axis bite block system. The base structure further solves the problem of interference with the path of radiation by providing longitudinal openings along the medial and lateral sides of the base structure. These features, thus arranged, allow free passage of the radiation beams through the openings of the base structure, providing unobstructed treatment to the side of the head or neck, from the posterior position, otherwise known as the posterior oblique treatment area. The advantage gained by mounting the vertical support member off the central axis, in the left or right superior positions on the base structure, is that this technique allows unobstructed treatment to be provided to the forehead or face, uniquely allowing treatment of an anterior oblique view.

It is another object of the present invention to provide a means for securing head rests from movement, by providing a trough in the base structure, sized to receive head rests interchangeably, but securely in the Base Structure. A leveling device in the base structure allows the bite block system to be adjusted and accurately leveled prior to treatment.

It is still another object of the present invention to provide a means for variable movement, and measurable, precision adjustment of position, and positional locking of the entire system, from the base structure to a free air passage bite block, that is placed in the mouth of the patient being treated.

These together with other objects and advantages which will become subsequently apparent reside in the details of construction and operation as more hereinafter described and claimed, reference being had to the accompanying drawings forming a part thereof, wherein like numerals refer to parts throughout.

DESCRIPTION OF THE PREFERRED EMBODIMENTS

Figure 2:
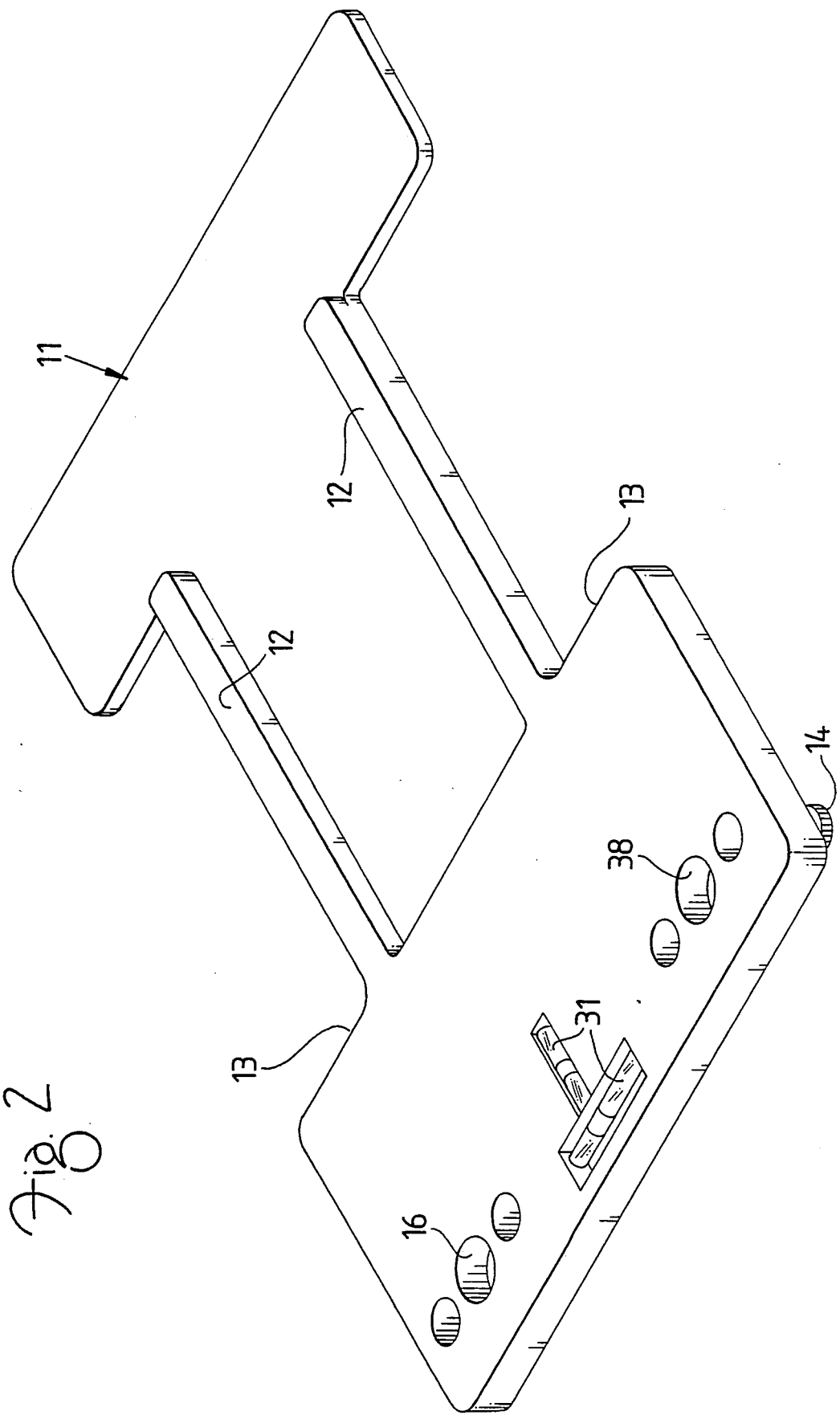
FIG. 2 is a schematic perspective view from the lateral side of the base structure portion of the invention.
Figure 4:
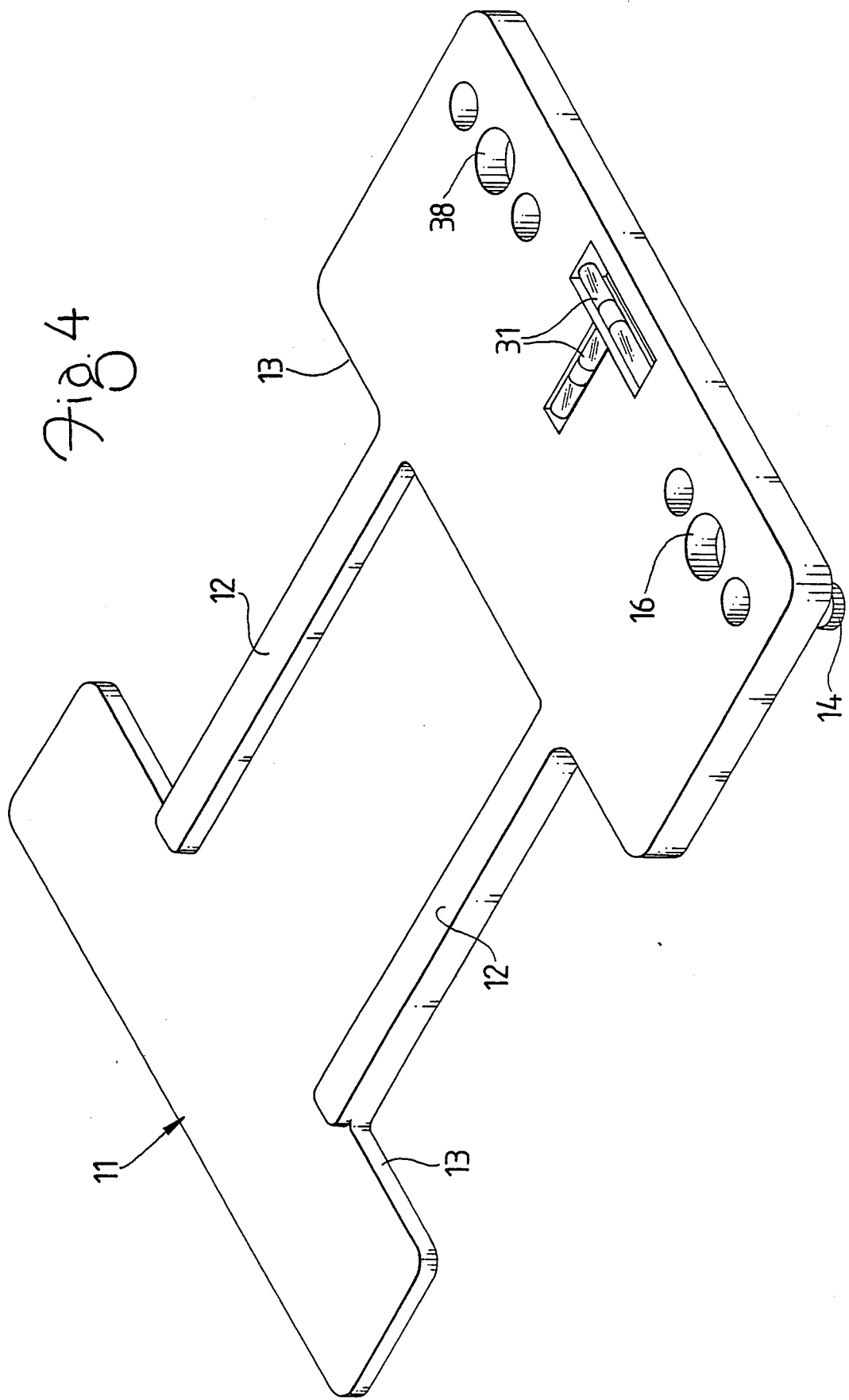
FIG. 4 is a schematic perspective view from the medial side of the base structure portion of the present invention.
Figure 5:
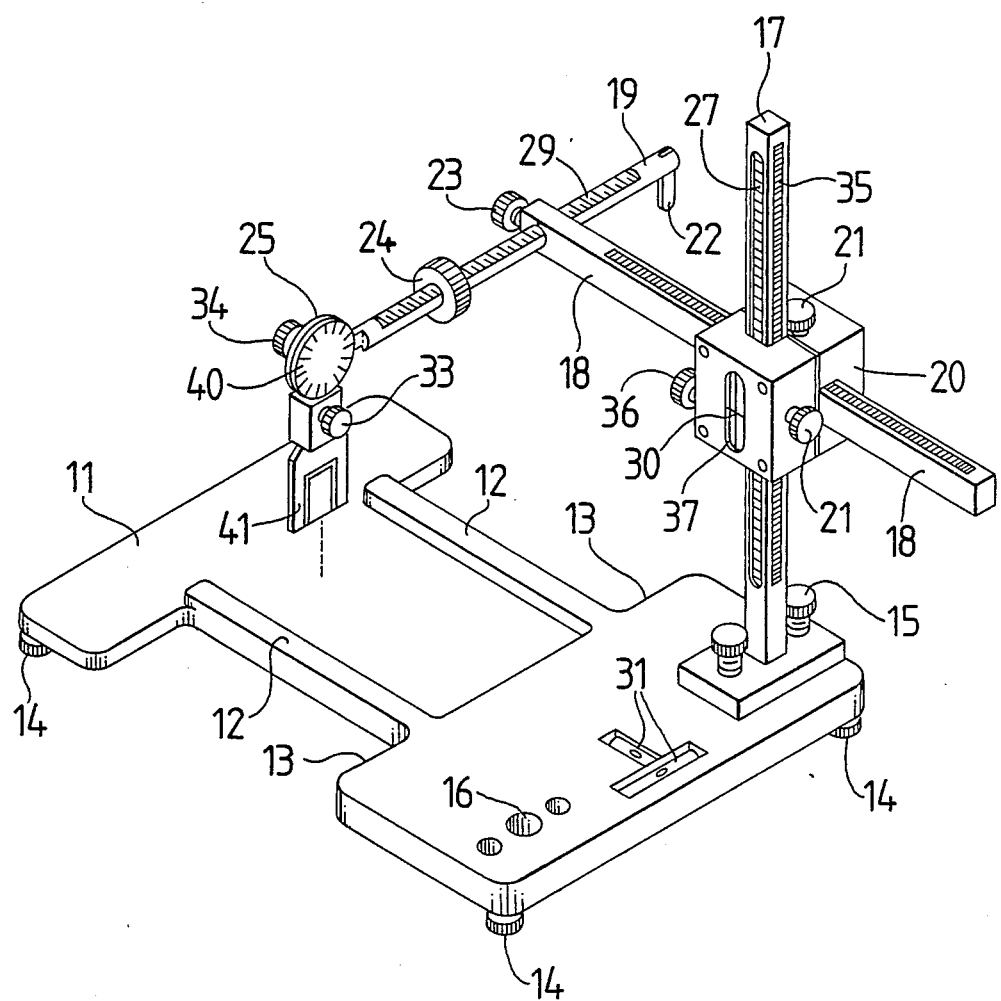
FIG. 5 is a perspective view of the complete structure.

Referring now to FIGS. 2 and 4 of the Drawings, an anterior-lateral off-axis bite block system, used as a head and neck immobilizer to maintain a specific position during treatments with radiation, according to the present invention, includes a bite block base 11, having a superior left mounting accomodation 16, and a superior right mounting accommodation 38, the base 11 features rounded corners and edges to provide safe use by the patient and the technologist. A needed and novel feature is provided by the two longitudinal raised members 12 that form a longitudinal trough on the base 11 for the purpose of receiving and securing from movement during treatment a removable head rest support, (not shown), the base 11 incorporates a recessed longitudinal and latitudinal bubble leveler 31 at the center of the superior end, manually adjustable non-skid leveling screws 14 may be selectively adjusted at the four corners of the bite block base 11 to achieve accurate leveling for the system.

The base 11 is provided with medial and lateral openings 13 indented to the edge of, and running the length of, the two longitudinal raised members 12, the described openings enable the unobstructed passage of radiation beams in the posterior oblique therapy position.

Referring now more particularly to FIG. 2 and 4 of the Drawings, it will be seen that a vertical member 17 (FIG. 3) may be selectively mounted to the base 11 in either the left 16 or right 38 superior mounting accommodations by fitting the base of the vertical support members 17 to the desired mounting accommodations 16 or 38, with the vertical support members 17 in the mounted position, the locking thumb screws 15 attached to the vertical support members 17 may be securely tightened by hand. By this arrangement, it will be seen and appreciated that rapid and versatile changes in the system positions may be accomplished by the Radiation Technologist without necessitating movement of the base 11, or movement of the patient being treated.

Figure 1:
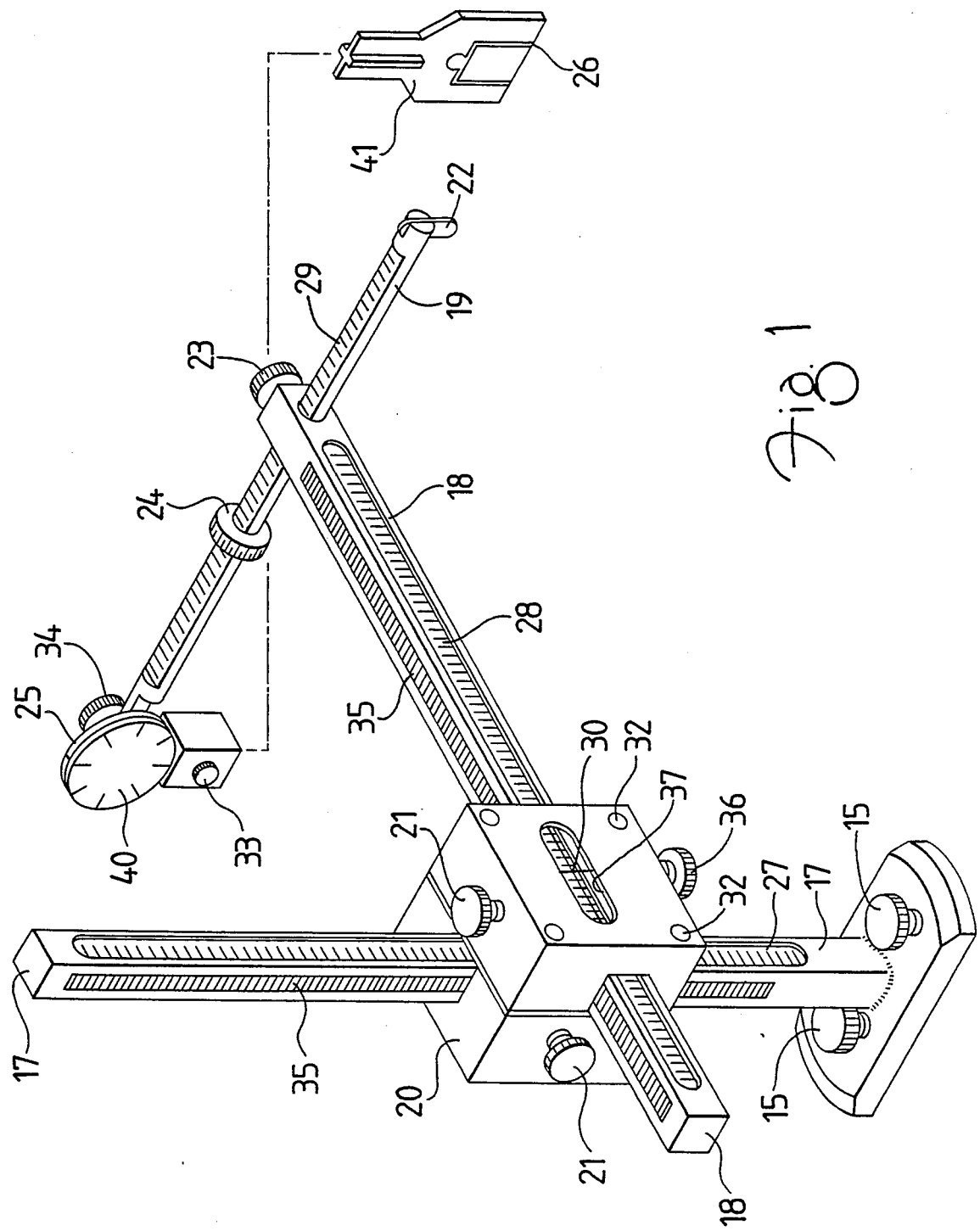
FIG. 1 is a schematic side elevational view similar to FIG. 3, but showing the horizontal support member, scale, and method of mounting.
Figure 3:
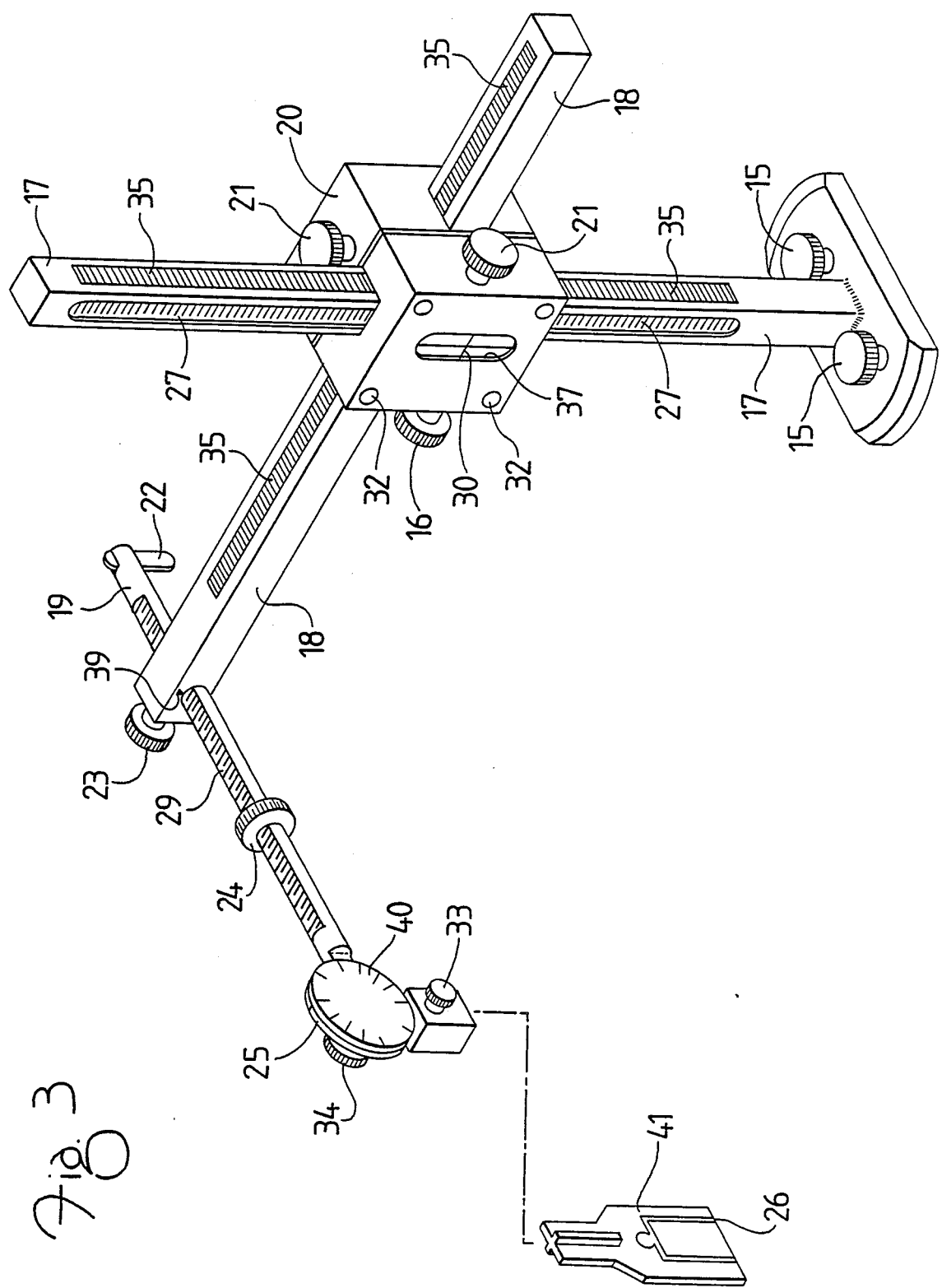
FIG. 3 is a schematic side elevational view similar to FIG. 1, but showing the vertical support member, scale, and method of mounting.

FIG. 3 of the drawings discloses a scale 27 applied in a slight recess in the left side of the vertical support member 17. FIG. 1 of the drawings disclose an identical scale 27 applied in a slight recess in the right side of the vertical support member 17. FIG. 1 also discloses a scale 28 applied in a slight recess in the horizontal support members 18, the vertical scale 27 and the horizontal scale 28 are applied to the functional lengths of the vertical support members 17 and the horizontal support member 18 and may be calibrated in millimeters, or any other precise measurement scale as elected optionally. The scale, 18 and 28, are designed to be luminescent, or may utilize other colors or means to show the scale, 18 and 28, clearly, so as to allow a precise adjustment and setting to be made by the Technologist prior to initiation of the radiation treatment. For repeat treatments, the prior measurements may be inscribed on the chart of the patient, thus permitting quick replication of the measurement settings, and eliminating the need for making new measurements prior to each treatment. As can be seen from FIGS. 1 and 3, the two piece vertical and horizontal member mounting block 20 incorporates a see-through aperture 37 on the medial and lateral sides which may additionally utilize magnifying lens installed in the aperture 37 to enable the scales 28 and 18 to be read easier. Measurement markers 30 are provided in the apertures 37 for more precise accuracy when reading the scales 28 and 18. It will be appreciated that the vertical and horizontal members mounting block 20 functions also as an adjustable and movable mount and guide, having geared turnscrews and adjusting knobs 21 which mesh with gear train 25 incorporated in the vertical member 17 and horizontal member 18, two-hand operated locking screws 26 are provided to enable the vertical member 17 and horizontal member 18 to be locked in the desired position. As can be readily seen in the drawings, the vertical and horizontal member mounting block 20 is constructed of two pieces, that when assembled and secured together, preferably by threaded allen-type bolts 32, installed in drilled and threaded holes in the corners of the left and right side of the mounting block 20, serves as the mount and guide for the vertical member 17 and the horizontal member 18.

Referring now more particularly to the transverse support member 19, it will be seen that the horizontal member 18 has a properly sized hole designed to receive the transverse support member 19, allowing adjustable movement, measurable by a scale 29, similar to 27 and 28. The transverse member 19 is flattened along the top side to receive the scale 29, a flat handle 22 is attached moveably in the slotted end of the transverse support member 19, allowing easy removal of the transverse support member 19 from the horizontal support member 18 in order that proper installation may be accomplished when changing positions of the system, for example, referring from the left superior position 16, (FIGS. 2 and 4) to the right superior position 38 and the reverse.

Referring again to FIGS. 1 and 3, the transverse support member 19 incorporates a sliding ring 24, having a scale in degrees on the outside circumference. The sliding ring 24 is keyed by a metal peg (not shown on drawing), on the inner circumference, which fits into a longitudinal groove (not shown on drawings), running the length of the scale 29, on the bottom side of the transverse support member 19, allowing the sliding ring 24 to be freely moved along the length of the transverse support member 19, thus, when the is moved radically rotated in either direction, the scale on the sliding ring 24, when placed close to the indicator mark 39 (FIG. 3) will indicate in degrees, the longitudinal oblique angle of the bite block mount 25, which is held in place by tightening the hand operated lock screw 23, in the bite block mount 25. When the proper angle is determined by the transverse support member 19, the hand operated locking screw 23 can be secured to hold the desired longitudinal angle of the bite block 41.

A particularly advantageous feature of the present invention is that the bite block mount 25 is threaded from the back, so as to receive a hand operated locking screw 34, which, when passed through the end mounting hole (not shown on drawings) on the transverse member 19, and screwed into the threads on the bite block mount 25, may selectively be tightened so as to hold the bite block mount 25 vertically, or in various desired latitudinal oblique positions as needed for radiation therapy. The radial dial 30 on the bite block mount 25 is calibrated and marked for adjustment of the vertical and latitudinal oblique positions. A unique feature of the bite block 41 is that the mounting end has a male cruciformed shape, which fits into a female cruciformed receptacle, resulting in an immoveable bite block mount 41, when the system is adjusted and tightened. Yet another unique feature is that the bite block mount 41, also has an enclosed dual built-in free air passage channel 16, and two smaller openings at the bottom edge of the bite block mount 41. This feature enables the patient to breath through the free air passage channel 26, overcoming the blockage caused by usage of dental impression material on the bite block mount 41, and in the mouth of the patient.

As can be understood from the above description and from the drawings, a radiation therapy bite block system according to the invention provides for: head and neck immobilization of all anterior and lateral positions of radiation treatment of the patient without interference with any part of the radiation beam; replication of anterior, anterior-lateral, anterior oblique, and posterior oblique positions of radiation treatment of the patient without interference with any part of the radiation beam.

The foregoing is considered as illustrative only of the principles of the invention. Further, since numerous modifications and changes will readily occur to those skilled in the art, it is not desired to limit the invention to the exact construction and operations shown and described, and accordingly all suitable modifications and equivalents may be resorted to, falling within the scope of the invention.

What is claimed as new is as follows:

1. A radiation therapy bite block system allowing treatment of all anterior and lateral positions, without interference of any part of the radiation beam, capable of fulfilling all head and neck immobilization requirements, and capable of replicating all head and neck treatment positions, comprising in combination:

a. a head and neck immobilizing bite block base with a means for left superior, and right superior off-axis immobilization system mounting;

b. a vertical support member, having a mounting base that is interchangeably fixable in the means for left superior or right superior off-axis immobilization system mounting;

c. a two piece vertical and horizontal mounting structure, having adjustable fastening means, and movably supported on the vertical support member;

d. a horizontal support member, sized to moveably fit into the two piece mounting structure, having an opening at one end thereof;

e. a transverse support member, sized to be supportably received by the opening in said one end of the horizontal support member, and movable axially and rotatably therewithin;

f. a bite block mount, having a cruciform shaped bite block stem receptacle which is mounted to one end of the transverse support member for positioning at a selectable point over the bite block base;

g. a removable bite block mouthpiece structure, having a cruciform shaped stem, mateable with the bite block stem receptacle, and disposable in the mouth of a patient during radiation therapy to facilitate off-axis immobilization of the patient's head and neck.

2. An improvement as defined in claim 1, wherein the bite block base comprises in combination:

a. a planar member having rounded corners and edges;

b. two longitudinal raised members disposed on said planar member to form a trough for selectively receiving a removable head rest support;

c. a recessed longitudinal and latitudinal bubble leveler affixed to said planar member arranged to facilitate level utilization of the system;

d. leveling means for achieving accurate leveling and minimizing slippage of the system;

e. two longitudinal outwardly opening recesses extending parallel to the two longitudinal raised members, defining two interference free passage areas for a radiation beam during posterior-oblique projections of radiation.

3. An improvement as defined in claim 1, wherein each of the support members includes a means for measurement and precision adjustment comprising in combination:

a. a scale divided in predetermined increments extending along a predetermined length of vertical support member;

b. a second scale extending along a predetermined length of the horizontal support member;

c. a third scale extending along a predetermined length of the transverse support member;

d. a keyed sliding ring having a fourth scale around the circumference thereof mounted on the transverse support member to indicate angular displacement of the transverse support member;

e. a radial dial, disposed on the bite block mount, and adapted for measured adjustment of vertical, lateral or medial bite block positions;

f. a flat handle, movably attached to the transverse support member distal said bite block mount for lateral, inferior, and superior movement of the transverse support member.

4. An improvement as defined in claim 1, wherein, the two piece vertical and horizontal mounting structure includes see-through apertures on the medial and lateral sides with magnifying means and measurement markers provided therein for ease of viewing and precision adjustment of the vertical and horizontal support members.

5. An improvement as defined in claim 1 wherein the removable bite block mouthpiece structure includes a plurality of channels, having openings at the edge of the wide-end of the removable bite block mouthpiece structure outside the area thereof which would, in use, be covered by the mouth.

6. An improvement as defined in claim 1 wherein said two piece vertical and horizontal mounting structure further comprises means for engaging said vertical support member and horizontal support member for selective relative movement therebetween to precisely reproducible positions.

* * * * *